United States Patent [19]

Williams

[11] Plant 4,426

[45] Jun. 12, 1979

[54] ROSE PLANT

[76] Inventor: Ernest D. Williams, 1510 Lebanon Ave., Dallas, Tex. 75208

[21] Appl. No.: 901,285

[22] Filed: Apr. 28, 1978

[51] Int. Cl.[2] ..... A01H 5/00

[52] U.S. Cl. ..... Plt./7

[58] Field of Search ..... Plt./7

*Primary Examiner*—Robert E. Bagwill

[57] ABSTRACT

The present miniature rose, subject of this disclosure, is primarily characterized by the basically white bud and flower and the unique blending or edging of petals with shades of soft to deep rose pink color.

1 Drawing Figure

1

The present invention relates to a new and distinct variety of hardy, dwarf, bush type rose plant of the miniature class; the variety being characterized — as to novelty — by white to near white buds and flowers with a portion of each upper petal surface shaded or overlaid with soft pink to deep rose pink color.

The variety is further characterized by:

An abundance of bloom with flowers borne singly or several to the stem in loose clusters.

Slight fragrance.

A plant which is vigorous, of rounded upright shape and with medium-small matt foliage with pointed leaflets; the buds and flowers being similar in form and size to Easter Morning (miniature — U.S. Plant Pat. No. 2,177).

The plant, which has a normal height of 12–14 inches or more, can easily be maintained at lesser height by occasional trimming.

A plant which grows and blooms satisfactory both in greenhouse and outdoors; is good for exhibition and as cut flowers.

The present variety of miniature rose was originated by me at my nursery located at Dallas, Tex., under conditions of careful control and observation, as a cross between Little Darling (Floribunda — U.S. Plant Pat. No. 1,581, expired) as the seed parent and Over the Rainbow (miniature — U.S. Plant Pat. No. 3,472) as the pollen parent.

Subsequent to origination of the variety I successfully reproduced it in my nursery located as aforesaid, by cuttings; the reproductions having run true in all respects.

The color photograph illustrates the variety, showing foliage, buds and flowers.

Referring now specifically to the new and distinct variety of miniature rose plant, the following is a detailed description thereof in outline; all major color plate identifications being by reference to the British Colour Council Horticultural Colour Chart, except where common terms of color definition are employed.

Type: Hardy, dwarf; bushy; seedling; greenhouse; outdoors; cut flowers; garden decoration; potted plant.

Class: Miniature. Variety name 'CARELESS MOMENT'.

Flowers: Continuity, continuous — repeat bloom all season. Fragrance, slight.

Quantity of bloom: Free bloom both outside and in greenhouse.

2

Bud: Peduncle — medium to long; slender; wirey; erect; medium green, sometimes tinted bronze (outdoors); hairs — several. Before calyx breaks, size — small.

Form: medium long; pointed with few foliaceous appendages and few or no hairs on surfaces of bud; with foliaceous parts extending beyond the tip of the bud equal to one-half or less of its length.

Color: medium green, occasionally tinted with bronze (outdoors).

*As calyx breaks.*—Color — near white to greenish white; opens; same general color with upper surface of each petal tinted or tipped with soft to deeper shades of rose pink.

*Size.*—Small.

Bloom:

*Size when fully open.*—Small, averaging about 35–40 cm (1½").

*Petalage.*—Double, averaging about 40–50 petals plus several petaloids, arranged regularly.

*Form.*—Full; high center at first, becoming more rounded, full; with petals rolled loosely outward, and later at maturity, rounded, full; with petals rolled loosely outward and downward. Open flowers usually show no stamens.

Petals: Thick; satiny on inside and outside surfaces.

*Shape—outside petals.*—Broad lanceolate (nearly round) with short acute tip; intermediate petals: broad lanceolate (nearly oval) with rounded tip; inside petals, lanceolate or broad lanceolate with rounded or small acute tip.

Color: Newly opened flower from a plant grown outdoors (April, 1978), Visalia, Calif.

*Outside petal.*—Outside surface — pale greenish at base blending into white or near white; inside surface — similar to outside surface then blending into shades of pink to rose pink, on petal tips of a shade or shades similar to Fuchsine Pink 627/3 and blending into shades similar to Fuchsine Pink 627/1, and at times almost as deep as Roseine Purple 629/2, the depth or shade of color depending upon intensity of sunlight. Color as shown in illustration is at deepest shading, being a deep rose to lavenderish pink. Note: Flowers grown in plastic greenhouse (same date as flowers described above and shown in color photo) are pale greenish white to white with a slight pink tinting on petal tip (lighter than flowers grown outdoors) of a shade or shades varying from near white through shades similar to Neyron Rose 623/3 to Fuchsine Pink 627/3.

*Intermediate petal.*—Outside surface — similar to outside petal. Inside surface — similar to outside petal but with less rose colored petal surface.

*Inner petal.*—Outside surface — similar to intermediate petal; inside surface — similar to intermediate petal. General color effect newly opened flowers — a bi-colored effect with both white and pink areas. Three days open — color similar to newly opened flower but petal tip on upper surface may have become deeper shade. Behavior — as flowers age the inside (upper) surface of petals may tend to deepen color. Spent petals drop off. Flower longevity (April, 1978) — plant in pot 10 days or longer. Cut flowers at living room temperature 5–7 days or longer.

Reproductive organs:

*Stamens.*—Few.

*Filaments.*—Varying length, whiteish, few.

*Anthers.*—Malformed (if present).

*Pollen.*—None.

*Pistils.*—Few.

*Styles.*—Short, bunched.

*Stigma.*—Nearly white.

*Ovaries.*—All enclosed in calyx.

*Hips.*—None.

*Sepals.*—Permanent; spear-shaped; recurved.

*Seed.*—None.

Foliage:

*Leaves.*—Compound of five (sometimes three or seven) leaflets; abundant; medium small; leathery; matt.

*Leaflets.*—Shape; broad lanceolate, nearly oval; apex acute; base rounded. Margin serrate. Color: medium green; new growth often tinted reddish. Rachis: medium strength; upper side may have a few tiny short hairs, grooved; underside sparsely thorny with few or no tiny prickles. Stipules: medium long; narrow to medium width, medium length narrow points which turn out usually at about 45 degrees or less.

Growth:

*Habit.*—Dwarf; bushy; upright; much branched.

*Growth.*—Vigorous.

*Canes.*—Medium; slender; sturdy.

*Main stems.*—Color; medium to deep green. Thorns: relatively few (3 to none per 10 cm of main stem). Fairly large, nearly straight, inclined slightly downward; color — tan or brown. Prickles — none; hairs — none.

*Branches.*—Color: medium green. Thorns: few; medium length; slender; nearly straight; inclined slightly downward. Color: tan. Medium to short oval base. Prickles: none. Hairs: none.

*New shoots.*—Color: green, often tinted reddish. Thorns: few or none. Prickles — none; hairs — none.

The miniature rose plant and its flowers as herein described may vary in slight detail due to climatic, soil and cultural conditions under which the variety may be grown; the present descriptions being of the variety as grown at Dallas, Tex. and Visalia, Calif.

The following is claimed:

1. A new and distinct variety of miniature rose plant of hardy, dwarf, bushy, upright, much branched habit, essentially as illustrated and described, characterized by buds and flowers of a basic white or near white color with the upper petal surfaces shaded, blended or tinted with light to deep pink color of varying hue and intensity, ranging from very soft shades of Neyron Rose to deeper shades of rose pink to lavenderish pink, depending upon conditions of culture and intensity of direct sunlight; the form and size of bud and flower resembling Easter Morning; and further characterized by a plant which is vigorous and relatively compact, said plant being easy to propagate from cuttings, with medium small, disease resistant matt foliage, an abundance of bloom with excellent keeping qualities, with flowers borne singly or several to the stem in loose clusters.

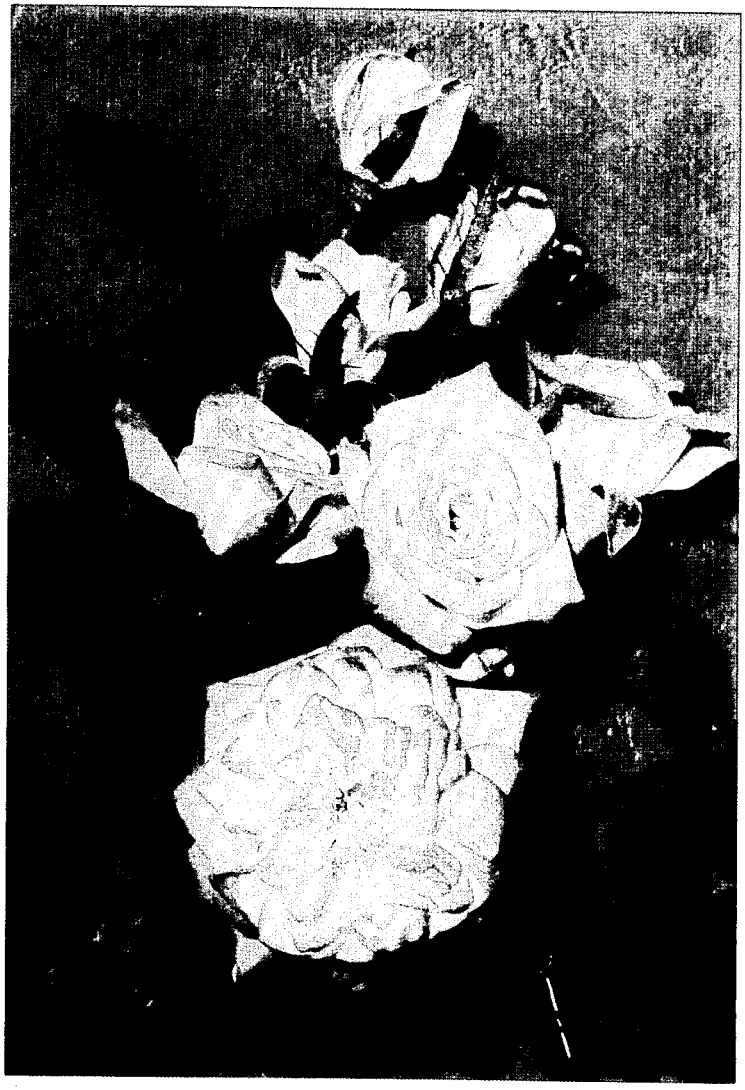

* * * * *